United States Patent [19]

Lehovec et al.

[11] Patent Number: 4,470,263

[45] Date of Patent: Sep. 11, 1984

[54] PELTIER-COOLED GARMENT

[76] Inventors: Kurt Lehovec, 202 S. Juanita Ave., Apt. 2-214, Los Angeles, Calif. 90004; Rose Shuttleworth, 1522 First St., Apt. M204, Coronado, Colo. 92118; Yussef A. Bedri, P.O. Box 3183, Riyad, Saudi Arabia

[21] Appl. No.: 196,599

[22] Filed: Oct. 14, 1980

[51] Int. Cl.³ ............................................. F25B 21/02
[52] U.S. Cl. ........................................... 62/3; 62/259.3
[58] Field of Search .................... 62/3, 259.3, 235.1; 128/379, 403; 150/2.3, 2.6

[56] References Cited

U.S. PATENT DOCUMENTS

| 2,798,493 | 7/1957 | Sukacev | 62/3 X |
| 2,798,494 | 7/1957 | Sukacev | 62/3 X |
| 2,919,735 | 1/1960 | Prietzsch | 150/2.3 |
| 2,991,627 | 7/1961 | Suits | 62/259.3 X |
| 3,132,688 | 5/1964 | Nowak | 62/3 X |
| 3,136,577 | 6/1964 | Richard | 62/3 X |
| 3,154,926 | 11/1964 | Hirschhorn | 62/259.3 X |
| 3,165,900 | 1/1965 | Huntington | 62/3 |
| 3,353,191 | 11/1967 | Dahly | 62/235.1 X |
| 3,548,415 | 12/1970 | Waters | 62/259.3 X |
| 3,943,726 | 3/1976 | Miller | 62/235.1 |
| 4,143,711 | 3/1979 | Beitner | 62/3 X |
| 4,204,543 | 5/1980 | Henderson | 150/2.3 |
| 4,280,330 | 7/1981 | Harris et al. | 62/3 |

FOREIGN PATENT DOCUMENTS 2652482  5/1978  Fed. Rep. of Germany ..... 62/235.1

Primary Examiner—Lloyd L. King

[57] ABSTRACT

This invention concerns heat relief by Peltier cooling. In one embodiment Peltier cells are attached to a garment with the cold plate of the Peltier cell in intimate thermal contact with the skin of the wearer of the garment. Heat generated by the Peltier cell is dissipated to the ambient from cooling fins. Heat pipes are used to conduct the heat to the fins, or to distribute the cooling across the skin.

9 Claims, 5 Drawing Figures

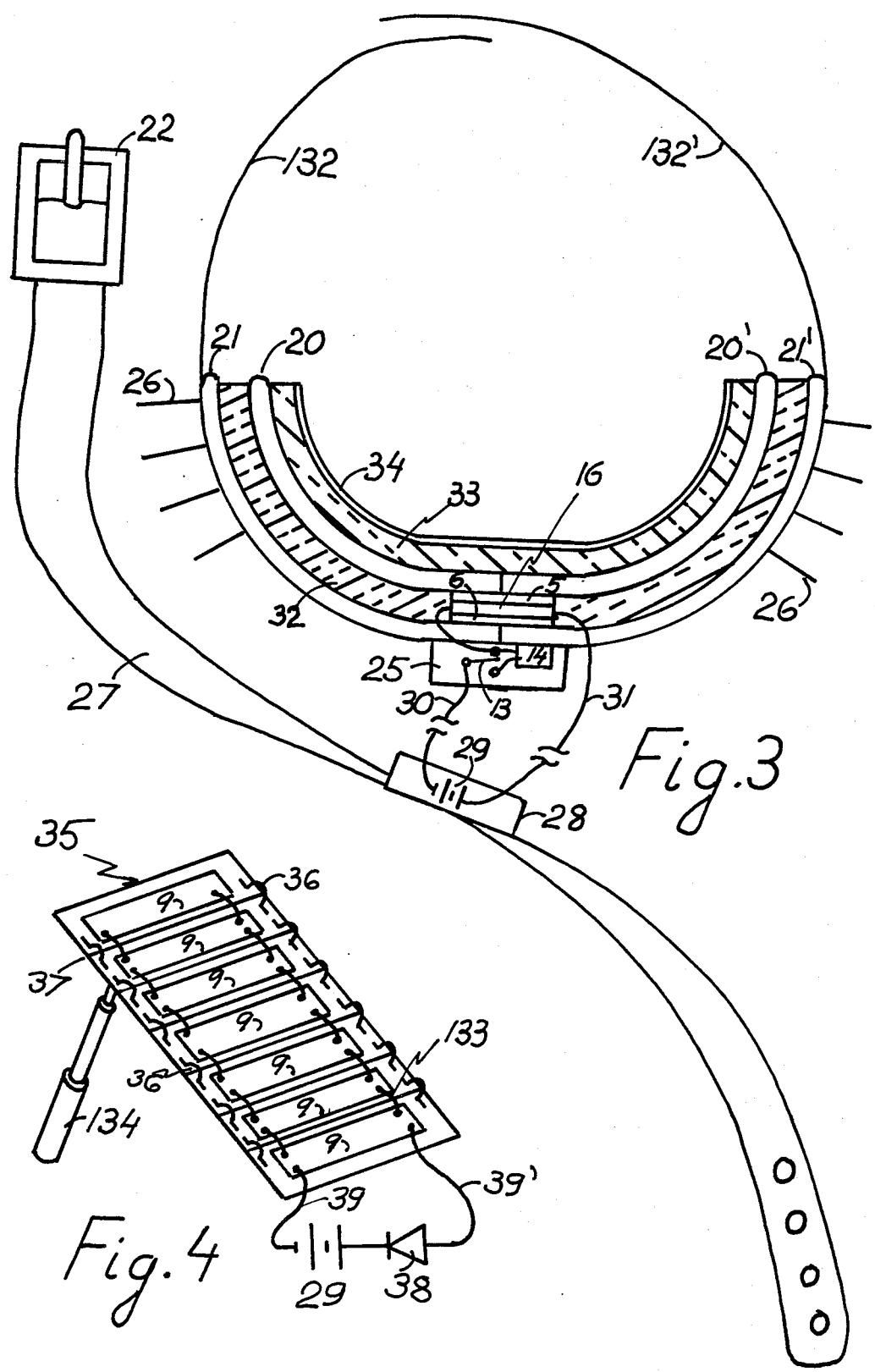

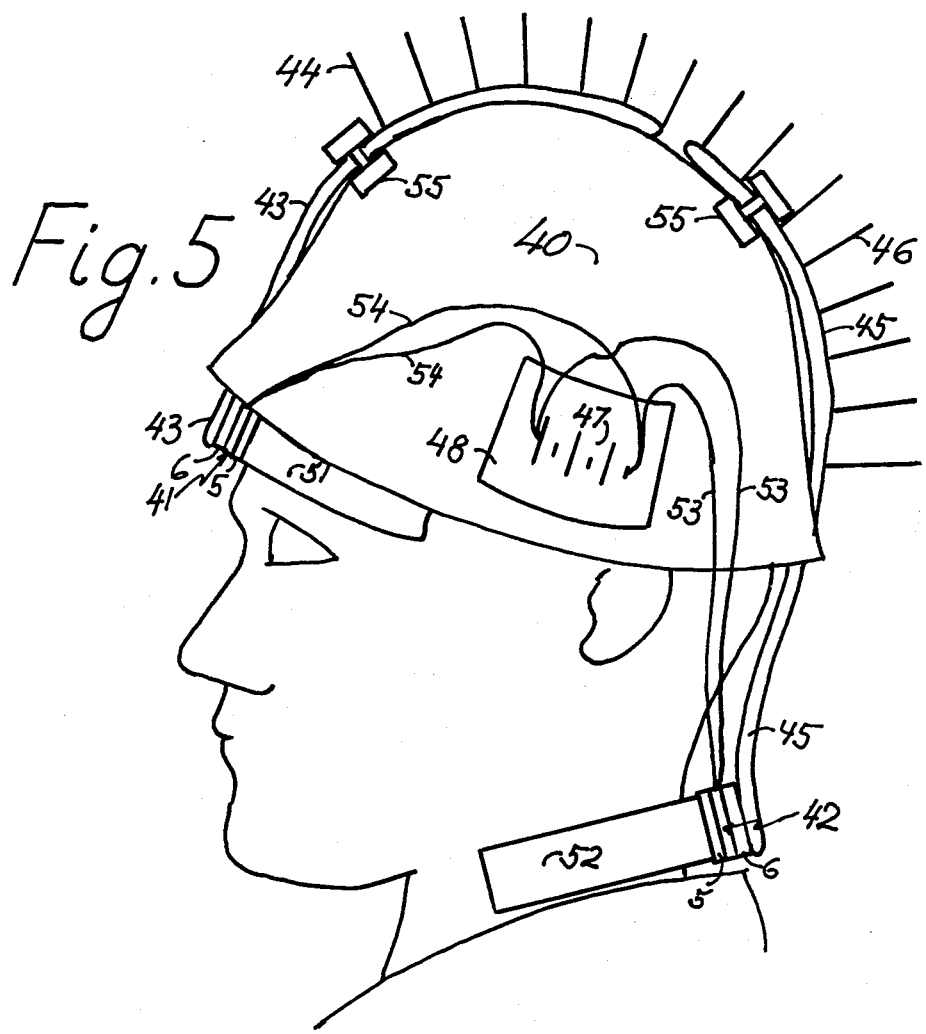

PELTIER-COOLED GARMENT

In other embodiments of our invention the Peltier cells are powdered by portable rechargeable batteries, or by solar cells carried by the person to be cooled. The rechargeable batteries are charged by portable solar cells.

BACKGROUND OF THE INVENTION

There is ample need for heat relief for humans in a hot ambient. In some cases heat relief provides merely comfort, e.g., in home, office, or car air conditioning. In other cases heat relief is a necessity for proper functioning of the human body, e.g., during re-entry of astronauts, during mine worker's rescue missions, and for fighter pilots in confined cockpits.

The metabolic rate of a human at rest is about 100 Watts, and it increases to about 300 Watts under a heavy work load. This additional energy generation rate is being dissipated to the environment mainly by the evaporation of perspiration. Excessive sweating leads to dehydration and loss of salts from the body, causing exhaustion.

In severe cases heat relief has been provided by specially designed garments containing a circulating cooling liquid, viz., "Water Cooled Garments: A Review", by Sarah A. Nunneley, published in Space Life Sciences 2 (1970) 335–360.

In less severe cases of merely providing comfort, such as in room air conditioning, there is an urgent need to conserve energy.

Tourists in hot countries, and outdoor manual workers in a hot ambient, e.g., construction workers in desert areas, would greatly benefit by personalized cooling means for comfort and increased work efficiency. The liquid cooled garments which are commercially available, e.g., from ILC Dover Corporation, Frederica, Del., are clearly unsuitable for these applications.

The present energy shortage requires energy savings. A major energy consumer is the air conditioning of entire enclosures, such as rooms, offices, and automobiles. Only a small fraction of this cooling is consumed by the inhabitants. By providing personalized cooling a very significant energy saving could be achieved.

It is an objective of this invention to provide a simple personalized cooling means.

It is another objective of this invention to provide a convenient garment providing cooling to the wearer.

It is still another objective of this invention to provide a cooling garment powered by a portable power source affixed to the garment of the wearer.

It is still another objective of this invention to provide a cooling garment powered by solar cells carried by the wearer.

It is still another objective of this invention to provide a cooling garment powered by portable rechargeable batteries in combination with transportable solar power means to recharge these batteries.

It is still another objective of this invention to provide a cooling garment or accessory which can be transformed into a heating garment or accessory by reversing the polarity of the current which activates said garment or accessory.

These and other objectives will become clear from the following brief description of the invention and its preferred embodiments.

SUMMARY OF THE INVENTION

Our invention provides cooling for humans by intimate thermal contact with the cold plate of a Peltier cell. In one embodiment of our invention the Peltier cell or cells are attached to a garment in such a way that the cold plate of the Peltier cell or cells contacts the skin of the wearer, while the heat generated by the Peltier cell is dissipated by means of cooling fins in good thermal contact with the hot plate of the Peltier cells. In a preferred embodiment heat pipes are used for the transport of heat from the hot plate to the cooling fins. A preferred location for cooling fins is the exterior of a helmet such as is worn by construction workers or motorcyclists. In another preferred embodiment a flat curved heat pipe is used to distribute the low temperature of the cold plate of the Peltier cell over a larger skin area. The preferred garments of this invention are head bands and neck bands carrying the Peltier cells.

In a preferred embodiment the Peltier cell or cells are powered by solar batteries mounted on the brim of a wide-brimmed hat, thus providing a self-powered portable unit. In another embodiment rechargeable batteries are used for powering the Peltier cells, with the batteries attached to a belt, or else to the aforementioned construction workers' helmet. A portable rack of solar cells is provided to recharge the batteries.

Reversal of the polarity of the current passed through a Peltier cell exchanges the hot and cold plates, thus providing heating for the skin, while absorbing cooling from the ambient by the fins. Thus the aforementioned cooling garments or fixtures can be transformed into heating garments or fixtures.

BRIEF DESCRIPTION OF DRAWINGS

FIG. 3 shows a top view of a Peltier cooled collar according to this invention for cooling forehead or rear of the neck, in combination with a belt carrying a battery pack for supplying power to the Peltier cell.

FIG. 4 illustrates a foldable solar cell rack for charging rechargeable batteries as used to power the Peltier cell in FIG. 3.

FIG. 5 shows a construction workers' helmet according to this invention, carrying heat dissipation fins connected by heat pipes to the hot plates of Peltier cells cooling forehead and neck of the wearer.

PREFERRED EMBODIMENT

Figure 1:
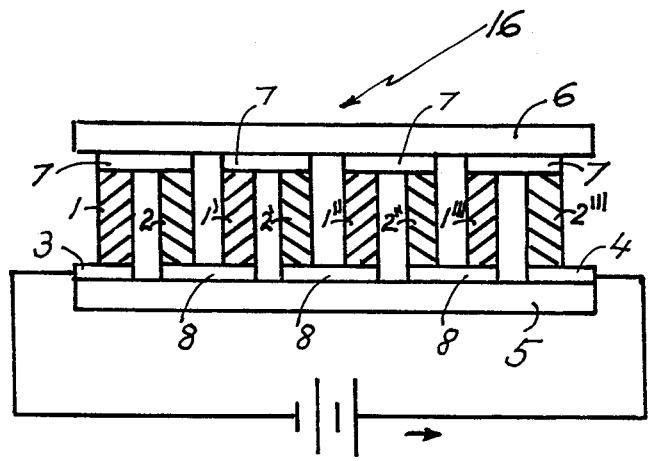
FIG. 1 illustrates a conventional Peltier cell.

Referring to FIG. 1, there is sketched a cross section of a Peltier cell 16 as is commercially available from several sources, e.g., Borg Warner Thermoelectrics, Chicago, Ill.; or Cambridge Thermionic Corporation, Cambridge, Mass. The Peltier cell comprises several columns 1, 1', etc., of an n-type semiconductor, and several columns 2, 2', etc., of a p-type semiconductor, interconnected by contacts 7 and 8. Direct current passed through the external contacts 3 and 4, with 4 positive, and 3 negative, heats the upper junctions 7 where the current flows from p- to n-type material, while it cools the lower junctions 8 where the current flows from n- to p-type material. Thus the upper insulator plate 6 becomes hot, while the lower insulator plate 5 is cooled.

Our invention provides for cooling of the body by means of Peltier cells in intimate thermal contact with portions of the body such that the cold plate faces the skin, and the hot plate faces the ambient. The skin temperature must not be lowered to less than about 17° C., in order to avoid cold pain. Furthermore, heat conduction from the core of the body to the skin occurs primarily through the blood stream, and this heat transfer is decreased by cardiovascular constriction when the skin temperature is too low. For a Peltier cell of about 1 square inch area, such as the Model 930-71 supplied by Borg Warner Thermoelectrics, at a current of the order of 1 ampere and a voltage of about 2 volts, the temperature difference between the hot and cold plates is about 20° C. at a cooling rate of 4 Watts and a hot plate temperature of about 40° C.

The Peltier cells are mounted on garments, or in fixtures, as will be illustrated in the following preferred embodiments.

Figure 2:
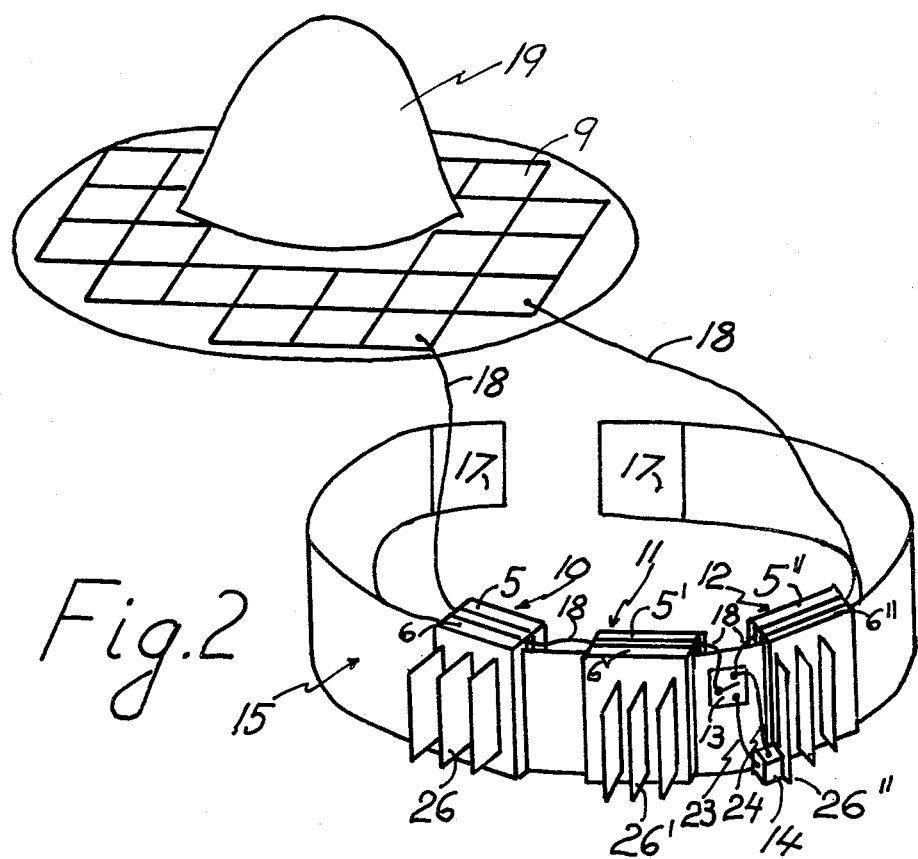
FIG. 2 shows a broad-brimmed hat carrying a solar cell array according to this invention, and a head band carrying three Peltier cells powered by said solar cell array.

Referring now to FIG. 2, there is shown an unfolded head band 15 containing the Peltier cells 10, 11, and 12. The hot plates 6, 6', and 6" of these Peltier cells face outward and carry the heat fins 26, 26', and 26", while the cold plates 5, 5', and 5" face inside to the forehead when the headband 15 is fastened around the head using the adjustable Velcro fastener 17. The Peltier cells are powered through leads 18 by the solar cell array 9 located on the wide brim of hat 19. The electric connection between the solar cell array and the Peltier cells includes the switch 13 mounted on the headband which allows inserting into the circuit through leads 23 and 24 the thermistor 14 which is mounted in close thermal contact with the heat dissipation fin 26". The thermistor has the following purpose: if the power to the Peltier cell were suddenly interrupted, heat from the hot plate would quickly transfer to the cold plate, causing a burning sensation on the skin. By inserting the thermistor 14 into the circuit, rather than interrupting the circuit, the current through the Peltier cells is reduced by the thermistor resistance, which reduces the cooling rate and the power dissipation in the Peltier cells, and thus the hot plate temperature. This in turn reduces the thermistor temperature, whose resistance thereby increases, causing further reduction in current, cooling rate, heat fin and thermistor temperatures, etc. In this manner a gradual cooling of the hot plate temperature and a gradual warming of the cold plate temperature can be achieved by appropriate choice of heat capacity, heat dissipation rate from the cooling fins, and thermistor characteristics. Electric power of seven watts used to operate the three Peltier cells is readily provided by silicon solar cells mounted on an eight inch wide brim, at noon time solar radiation. While the cooling rate of about 15 Watts achieved with three Borg Warner Model 930-71 Peltier cells under such operating conditions is only a small fraction of the metabolic rate of rest, we have, nevertheless, experienced a significant degree of comfort by this forehead cooling.

A considerably larger solar cell array can be accomodated by a stationary structure such as a beach umbrella. Such a solar cell array can thus power more Peltier cells, arranged, e.g., on a head and a neck band.

FIG. 3 shows a top view of another preferred embodiment for a head or neck cooling collar, providing Peltier cooling. In this embodiment a single Peltier cell 16 is arranged in such a manner that its cold plate 5 connects to the bent flat heat pipes 20, 20', while its hot plate 6 connects to the bent flat heat pipes 21 and 21'.

The heat pipes 20 and 20' are curved to fit the forehead or the neck, as the case may be. The space between the heat pipes is filled with a material 32 of low heat conductance, while the concave surface of the heat pipes 20 and 20' is lined with a resilient, thermally conducting layer 33. This resilient material can be made from foam rubber vacuum impregnated with heat conducting grease. A metallized cloth layer 34 which lines the resilient material 33 contacts the skin when the garment is worn. The box 25 contains the switch 13 and thermistor 14 combination discussed in connection with FIG. 2. The heat fins 26 dissipate the heat from the outer heat pipes 21 and 21'. The belt 27 with buckle 22 carries the compartment 28 which houses a rechargeable battery 29 for powering the Peltier cell 16 through wires 30 and 31. The bands 132, 132' are used to attach the Peltier cooling arrangement of FIG. 3 to the forehead or to the rear of the neck, as the case may be. The single Peltier cell 16 in FIG. 3 is operated at substantially higher current levels, i.e., several amperes, than are the cells 10, 11, or 12 in FIG. 2, yet the heat pipes 21, 21' keep the hot plate temperature at about 35° C. at an ambient temperature of 25° C.

FIG. 4 shows a rack 35, carrying solar cells 9, supported by a collapsible shaft 134, with hinges 36 which permit the rack to be folded along the lines 37. The folded solar cell rack fits into an attache case for ease of transport. The solar cell rack 35 charges the battery 29 of FIG. 3 when discharged, through leads 39 and 39' over rectifier 38. The leads 133 connect the solar cells in the various sections of rack 35.

FIG. 5 shows another preferred embodiment of the invention, to which a construction workers' helment 40 is used as support for the Peltier cells 41 and 42. The cold plates 5 of these Peltier cells connect to curved flat heat pipes 51 and 52 to provide cooled forehead and neck collars similar to that shown in FIG. 3. The heat pipes 51 and 52 distribute the cooling action of the Peltier cells 41 and 42 over larger skin area. The heat from the hot plate 6 of the Peltier cell 41 which cools the forehead is carried by the heat pipe 43 to the heat dissipating fins 44 on the top of the helmet. Similarly, the heat pipe 45 conducts the heat from the hot plate 6 of the Peltier cell 42 which cools the neck to the heat fins 46 on the top of the helmet. The heat pipe 45 is shaped to press the cooled collar 52 against the neck. The heat pipes 43 and 45 are attached to the helmet 40 by clamps 55. The Peltier cells are powered through leads 53 and 54 by a battery pack 47 contained in a compartment 48 of the helmet.

As there are many variations of our invention, it should be understood that our invention is not limited by the special embodiments here described, but encompasses all personalized cooling means for warm blooded species, man or animal, using Peltier cells, which are defined by the following claims.

We claim:

1. A cooling means for a person, said cooling means comprising
   (i) at least one Peltier cell,
   (ii) means to attach said at least one Peltier cell to said person,
   (iii) an electric power supply for said at least one Peltier cell, said electric power supply carried on an adornment worn by said person,
   (iv) the cold plate of said Peltier cell in intimate thermal contact with a portion of said person, said intimate thermal contact excluding gaseous and liquid layers interposed between said cold plate and said portion of said person, and (v) means for dissipating the heat from the hot plate of said Peltier cell, said means for heat dissipation comprising ambient exposure of a cooling fin arrangement of area larger than the area of said hot plate, with means other than forced cooling for transport of said heat from said hot plate to said cooling fin arrangement.

2. The cooling means of claim 1 whereby said means to attach is a head gear.

3. The cooling means of claim 1 whereby said electric power supply is at least one solar cell.

4. The cooling means of claim 2 whereby said electric power supply is at least one solar cell attached to said head gear.

5. The cooling means of claim 1 whereby said means for dissipating the heat from said hot plate include a metal sheet extending laterally beyond said hot plate.

6. The cooling means of claim 1 whereby said means for transport of heat from said hot plate to said cooling fin arrangement is a heat pipe.

7. The cooling means of claim 1 whereby said electric power supply is a rechargeable electric battery with provision for charging said battery by a portable array of solar cells.

8. A Peltier cooled head gear comprising (i) at least one Peltier cell with means to press the cold plate of said Peltier cell against a portion of the forehead, (ii) means inserted between said cold plate and said portion of the forehead to spread the temperature of the cold plate along a more extended portion of said forehead, (iii) extensions from the hot plate of said Peltier cell to dissipate the heat from said hot plate to the ambient, and (iv) a solar cell power supply for said Peltier cell mounted on a substantially horizontal extension of said head gear.

9. A cooling means for a person, said cooling means comprising (i) at least one Peltier cell, (ii) means to attach said at least one Peltier cell to said person, (iii) an electric power supply for said at least one Peltier cell, said electric power supply carried on an adornment worn by said person, (iv) the cold plate of said Peltier cell in intimate thermal contact with a portion of said person, said intimate thermal contact excluding gaseous and liquid layers interposed between said cold plate and said portion of said person, and, (v) means for dissipating the heat from the hot plate of said Peltier cell, said means for heat dissipation comprising ambient exposure of a cooling fin arrangement of area larger than the area of said hot plate, with means other than forced cooling for transport of said heat from said hot plate to said cooling fin arrangement including provisions for gradually reducing the power supplied to said Peltier cell, said provisions consisting of the insertion of a thermistor in the electric circuit connecting said power supply to said Peltier cell, said inserted thermistor reducing instantaneously the power supplied to said Peltier cell, thus causing a reduction of the temperature of the hot plate of said Peltier cell, said thermistor in thermal contact with said hot plate so that the resistance of said thermistor increases as said hot plate temperature is reduced, thereby gradually reducing the power supplied to said Peltier cell subsequent to said instantaneous reduction.

* * * * *